United States Patent [19]

Miller et al.

[11] Patent Number: 4,748,562

[45] Date of Patent: * May 31, 1988

[54] PORTABLE CIRCUIT AND METHOD FOR PERFORMING A TIME STUDY AND ANALYSIS OF BODILY CHARACTERISTICS

[75] Inventors: Joseph M. Miller; Stephen W. Fannin; Paul R. Steiner, all of Akron; Bruce C. Taylor, Kent, all of Ohio

[73] Assignee: Akron City Hospital, Akron, Ohio

[*] Notice: The portion of the term of this patent subsequent to Oct. 21, 2003 has been disclaimed.

[21] Appl. No.: 910,253

[22] Filed: Sep. 19, 1986

Related U.S. Application Data

[63] Continuation of Ser. No. 491,455, May 4, 1983, Pat. No. 4,618,929.

[51] Int. Cl.⁴ .......................... G06G 7/60; A61B 5/05; A61B 5/00
[52] U.S. Cl. ...................................... 364/415; 128/631; 128/635
[58] Field of Search ................ 364/415; 128/631, 635; 374/438, 444

[56] References Cited

U.S. PATENT DOCUMENTS

| | | | |
|---|---|---|---|
| 3,889,255 | 6/1975 | Pettersen | 340/347 CC |
| 4,109,527 | 8/1978 | Goode, Jr. | 73/343.5 |
| 4,319,189 | 3/1982 | Cullun, Jr. et al. | 324/208 |
| 4,326,535 | 4/1982 | Steffel et al. | 128/631 |
| 4,594,665 | 6/1986 | Chandra et al. | 364/422 |
| 4,618,929 | 10/1986 | Miller et al. | 364/415 |

OTHER PUBLICATIONS

G. Sanders, W. H. Ko, R. Jones and S. Vamvakas—*A Solid State Portable Gastroesophageal Reflux pH Recorder* (Abstract in Engineering in Medicine and Biology, 33rd Annual Conference, Washington, D.C. Oct. 1, 1980), sponsored by Alliance for Engineering in Medicine and Biology, Publisher: Institute for Electronic Engineers 1980-p. 54.
*Flexible pH Electrode for Esophageal and Gastro-Intestinal Research*, Microelectrodes, Inc., 1979.
*Esophageal Disorders: Pathophysiology and Therapy*, ed. T. R. DeMeester and D. B. Skinner, "Instrumentation for the Automatic Recording and Analysis of Esophageal pH", pp. 133–141, (1985).

Primary Examiner—Joseph Ruggiero
Assistant Examiner—Charles B. Meyer
Attorney, Agent, or Firm—Renner, Kenner, Greive, Bobak & Taylor

[57] ABSTRACT

A portable circuit and method for performing a time study and analysis of bodily ionic characteristics as esophageal pH includes a transducer 11 for measuring pH and generating a proportional analog signal and an interface 12 for converting this signal into a representative digital signal including offset and gain controls 23,24 for permitting correction for transducer 11 calibration drift during the study period. A processor 14 receives and stores all digital signals for rapid transmission to a data analysis after the study period is ended. Esophageal pH values are measured and stored for a plurality of pre-study and post-study known conditions.

5 Claims, 2 Drawing Sheets

PORTABLE CIRCUIT AND METHOD FOR PERFORMING A TIME STUDY AND ANALYSIS OF BODILY CHARACTERISTICS

This application is a continuation of application Ser. No. 491,455 filed May 4, 1983, now U.S. Pat. No. 4,618,929.

TECHNICAL FIELD

The present invention relates generally to a device for monitoring over an extended period of time bodily ionic characteristics. More particularly, the present invention relates to a completely portable circuit and a method for the periodic sampling and storing of bodily ionic concentrations, such as esophageal pH and the subsequent automatic processing of such data.

BACKGROUND ART

It has long been established that the continuous monitoring of various bodily ionic characteristics over extended periods of time provides data useful in the evaluation of disease. For example, diagnosis of gastroesophageal disorders, such as inflammatory disease or lower esophageal sphincter incompetence, may be made by the monitoring of esophageal pH over time. The earlier devices developed to perform such monitoring employed an electrode inserted through the nasal passage into the esophagus, a reference electrode in contact with the patient's skin, an electrical shock isolation module through which the signal from the electrodes and the patient were electrically isolated from monitoring instruments, and a pH meter and recording apparatus receiving, displaying and recording the isolated signal.

These devices effectively tether the patient to the pH meter and recorder because the electrodes and pH meter must be wired together by electrical conductors. With such a restricted range of movement, the patient's activities must be similarly circumscribed, resulting in data, generally known as a reflux pattern, that is not usually a true reflection of what generally occurs during the patient's ordinary activities.

More recently developed devices employed in the monitoring of pH in the distal esophagus have attempted to overcome this significant deficiency by radiotelemetering pH data from portable transmitting equipment carried by the patient to stationary radio receiving and recording instruments. One such device converts the esophageal pH signal to one that can be transmitted using a commercially available electrocardiogram (ECG) signal radiotelemetry system. Although this approach does permit the patient a much greater zone of freedom of movement than afforded by earlier devices (in the range of several hundred feet), and consequently does result in somewhat more accurate reflux patterns, the patient's mobility is still restricted.

Several additional drawbacks exist in known systems for monitoring esophageal pH over extended periods of time. The output signals from certain pH electrode types, as the renowned two millimeter diameter glass electrode, have a tendency to drift over extended periods of operation, introducing varying errors in the resulting reflux patterns. Inasmuch as different pH electrode types possess differing electrical output characteristics, heretofore monitoring systems were limited to operation with one type of pH electrode with which they were designed to operate. Also significant is that existing esophageal pH monitoring systems universally provide a reflux pattern in the form of a waveform output from a strip-chart recorder which require "reading" and interpreting by persons possessing a specialized and high level of skill. The scarcity of such trained medical personnel makes this task an additional burden and often results in undesirable delays in reaching a diagnosis.

DISCLOSURE OF THE INVENTION

It is, therefore, an object of the present invention to provide a device and method for monitoring over an extended period of time a bodily ionic characteristic where the device is completely portable and is not tethered by wires or electromagnetic signals to a remote data recorder.

It is a further object of the present invention to provide a device and method for monitoring over an extended period of time a bodily ionic characteristic, as set forth above, which includes an economical and lightweight data recorder for storing ionic concentration data, such as pH, in a form compatible with a digital computer.

It is yet a further object of the present invention to provide a device and method for monitoring over an extended period of time a bodily pH characteristic, as set forth above, which will account for calibration drift in the pH electrodes.

It is still a further object of the present invention to provide a device and method for monitoring over an extended period of time a bodily pH characteristic, as set forth above, which is suitable for use with different types of pH electrodes.

It is another object of the present invention to provide a device and method for monitoring over an extended period of time a bodily ionic characteristic, as set forth above, the output from which may be received and directly analyzed by a digital computer.

It is yet another object of the present invention to provide a device and method for monitoring over an extended period of time a bodily ionic characteristic, as set forth above, in which a digital computer is utilized to perform initial analysis of the stored pH data.

These and other objects and advantages of the present invention over existing prior art forms will become more apparent and fully understood from the following description in conjunction with the accompanying drawings.

In general, a circuit for monitoring over an extended period of study time a bodily ionic characteristic includes a transducer for measuring the ionic characteristic and generating an analog signal proportional thereto, and an interface for receiving the analog signal from the transducer and converting the analog signal into a representative digital signal, the interface including an adjustment circuit for permitting correction for drift in calibration of the transducer during the study period. A processor receives the digital signal, and at preselected occasions over the extended period of time samples and stores the digital signal, and upon the conclusion of the extended period of time rapidly transmits all the stored digital signals to a data analysis device.

A method for monitoring over an extended period of study time a bodily ionic characteristic includes the steps of determining and preserving the ionic characteristic for a plurality of pre-study and post-study known conditions, measuring the ionic characteristic and storing a representative digital signal at preselected occasions during the study period, and thereafter rapidly transmitting these stored digital signals to a data analysis device.

PREFERRED EMBODIMENT FOR CARRYING OUT THE INVENTION

Figure 1:
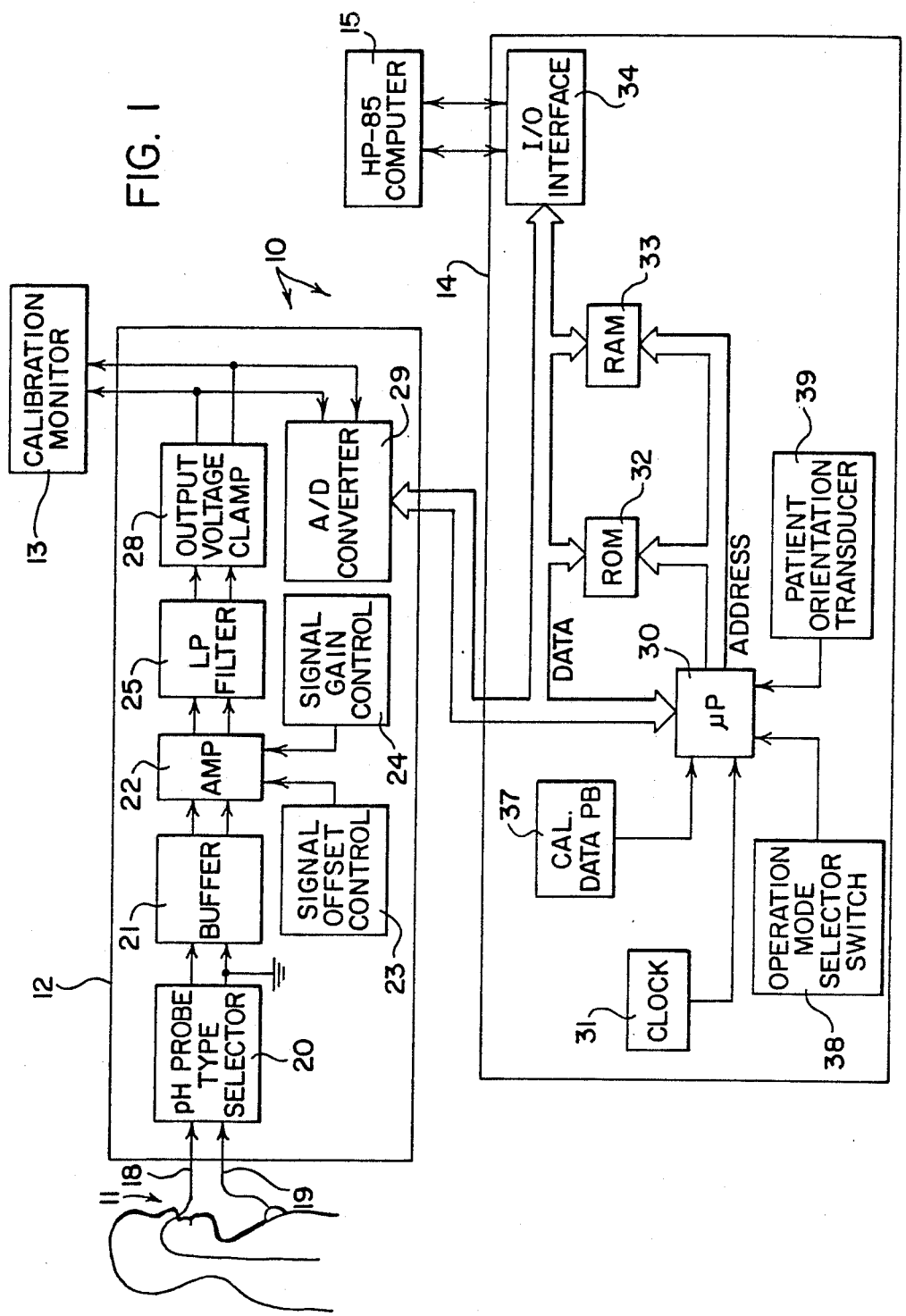
FIG. 1 is a block diagram of an exemplary portable pH monitoring device in accordance with the concepts of the present invention, also illustrating in block form a calibration voltmeter and computer for data analysis.

FIG. 1 illustrates a circuit generally indicated by the numeral 10, which also embodies a method for monitoring over an extended period of time a bodily ionic characteristic, pH concentration. Circuit 10 broadly includes pH monitoring transducer 11, interface 12 which may communicate with calibration monitor 13, and processor 14 which may communicate with computer 15.

Monitoring transducer 11 (hereinafter called "transducer 11") may be any transducer which furnishes a signal one of whose electrical characteristics, such as voltage, is proportional to the measured ionic characteristic, in the present example, pH. When monitoring esophageal pH, transducer 11 may include esophageal pH electrode 18 and a reference pH electrode 19. Esophageal pH electrode 18 may be a two millimeter diameter electrode of glass, antimony or other known type, and is usually inserted through the patient's nasal passage into the esophagus and then positioned approximately five centimeters proximal to the lower esophageal high-pressure zone. Reference pH electrode 19 may be any suitable calibration electrode as those utilized with electrocardiographs for attachment to the patient's skin.

Interface 12 permits usage of circuit 10 with several different types of pH monitoring transducers, provides for correction of calibration drift in transducer 11 over the period of any study, and converts the analog output signal from transducer 11 into a digital signal suitable for receipt by processor 14. In order to perform these functions interface 12 may include pH probe type selector 20, buffer 21, amplifier 22 with its associated signal offset control 23 and signal gain control 24, low pass filter 25, output voltage clamp 28 and analog-to-digital (hereinafter called "A/D") converter 29.

Buffer 21 may be a conventional operational amplifier having unity gain to isolate the signal from electrode 11 and the patient from the remaining circuitry. pH probe type selector 20 receives esophageal pH electrode 18 and reference pH electrode 19 and interconnects the electrode conductors to the inverting and non-inverting input terminals of the buffer 21 operational amplifier (not shown) through a slide or other suitable switching mechanism that permits the conductor input terminal polarity to be reversed, thereby permitting the use of different pH electrode types (such as glass and antimony) with circuit 10.

Amplifier 22 which also may be a conventional operational amplifier, receives the output signal from buffer 21 and amplifies the same for further processing. In order to permit proper calibration as will be discussed further hereinbelow, amplifier 22 should include signal offset control 23 and signal gain control 24 (both of which may be conventional potentiometers) for variable adjustment of the D.C. voltage offset and gain of the output signal from amplifier 22.

Low-pass filter 25 receives the output signal from amplifier 22 and conditions it by attenuating the high frequency components thereof, whereupon the conditioned signal is held by diodes or other suitable circuitry within output voltage clamp 28 to a maximum voltage compatible with A/D converter 29, typically 5 volts.

During calibration of circuit 10 with the selected transducer 11 a calibration monitor 13 is connected to the output of output voltage clamp 28. Calibration monitor 13 may be any device or circuit that furnishes the person performing the calibration a quantitative indication of the signal characteristic proportional to pH. Where, as in the example herein, voltage magnitude is selected as this electrical characteristic, a conventional voltmeter of sufficient impedance to avoid circuit loading effects may be utilized as calibration monitor 13.

A/D converter 29 may be any conventional A/D signal converter having a number of bits sufficient to provide the desired signal resolution. For purposes of monitoring esophageal pH, it has been found adequate to use 7 bits, providing 128 descrete pH levels, or 8 bits, providing 256 descrete pH levels. 8-bit A/D converters, such as a model ADC 0801 manufactured by National Semiconductor of Santa Clara, Calif., are readily commercially available and may be utilized as A/D converter 29.

Processor 14 controls pH and related data acquisition and storage during both the calibration phase and study period, further elaborated upon hereinafter, and supervises transmission of this data to computer 15 for further analysis. In order to perform these functions processor 14 may include microprocessor 30, clock 31, read-only-memory 32 (hereinafter called "ROM 32"), read-addressable-memory 33 (hereinafter called "RAM 33"), I/O interface 34, and several additional data input or control devices as calibration data pushbutton 37 (hereinafter called "pushbutton 37"), operation mode selector switch 38 (hereinafter called "switch 38"), and patient orientation transducer 39.

Although microprocessor 30 may be selected from any of the vast multitude of commercially distributed microprocessors, for optimum performance it should preferably incorporate an internal word-size architecture having at least the same number of bits as is required for acceptable pH resolution. In the instant example, an 8-bit microprocessor such as the model CDP 1802 manufactured by RCA Corporation's Solid State Division of Somerville, N.J., may be successfully utilized. Where microprocessor 30 does not include an on-board clock to control timing of its operations, an external clock 31 as provided by the manufacturer will be necessary.

Both ROM 32 and RAM 33 may be chosen from any of the numerous ROMs and RAMs presently available and should preferably be organized with each byte having a number of bits compatible with that of microprocessor 30, 8-bits in the present example. ROM 32 must possess sufficient byte capacity to store the program microprocessor 30 uses to direct the noted activities. RAM 33 must possess at least sufficient byte capacity to store all data recorded during the study period. Where data is to be sampled four times per minute and a study period of 24 hours is desired, RAM 33 must have a capacity of at least approximately 6000 bytes.

Memory capacity slightly larger than the minimum will allow data acquisition for the usual variation in the duration of the study period. In the particular instance described, a 2000 byte capacity ROM 32 and an 8000 byte capacity RAM 33 have been successfully utilized with circuit 10.

In order to communicate with external devices such as computer 15, processor 14 will include suitable input-/output interfacing circuitry, such as I/O interface 34. I/O interface 34 may be adapted to conform to any protocol, as that of the well-known RS232 serial communication, so long as it is compatible with the communications capability of computer 15. Conventional multi-conductor addressing and data buses are furnished between microprocessor 30, ROM 32, RAM 33, and I/O interface 34 as is understood by the skilled artisan.

Pushbutton 37 may be any single-pole, momentary contact pushbutton switch. Switch 38 may be a conventional two-pole, two position, maintained contact selector switch. Patient orientation transducer 39 is utilized to input information regarding the additudinal position of the patient and may be a two-pole, two position, maintained contact switch where such information is to be manually input by the patient, or any conventional position sensitive switch having distinct switch closures to indicate whether the patient is upright or supine, as a commercially marketed mercury position switch.

Circuit 10, with appropriate I/O interface 34 circuitry, will operate as delineated hereafter with any computer 15 whether it be a mainframe, minicomputer or microcomputer. Inasmuch as today's microcomputers are fully capable of performing any desired analysis of the gathered pH data, it has been found convenient both from an economic and portability standpoint to employ a microcomputer such as a model HP-85 made by the Corvallis Division of Hewlett Packard, Inc. in Corvallis, Oreg., to perform the desired functions.

Figure 2:
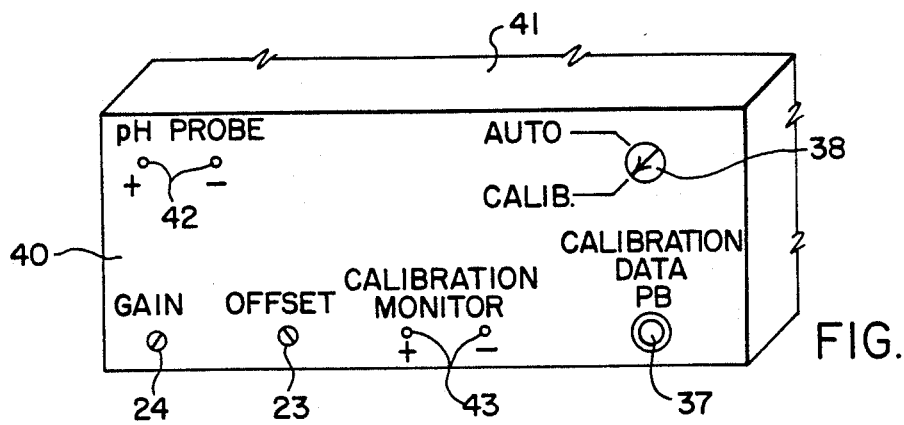
FIG. 2 is a plan view of an exemplary external control panel for the portable pH monitoring device.

FIG. 2, particularly useful when visualizing the patient's use of circuit 10, presents a plan view of an exemplary external control panel 40 on one end of a housing 41. Panel 40 carries all patient accessible controls and presents the terminals 42 into which pH electrodes 18 and 19 are inserted, the terminals 43 through which calibration monitor 13 is connected to interface 12, recessed signal offset control 23, recessed signal gain control 24, pushbutton 37 and switch 38. All these controls, in addition to the remaining portions of circuit 10 and a power supply suitable for powering circuit 10 throughout the period of study, are contained within housing 41, whose small dimensions and light weight permit it to be secured to the patient's belt or waistband by means not relevant hereto throughout the period of the pH study.

Operation of circuit 10 is straightforward. pH electrodes 18 and 19 are suitably applied to the patient and connected through terminals 42 to the remainder of circuit 10. Thereafter, interface 12 continuously converts the instantaneous analog magnitude of the desired pH characteristic into a representative digital signal suitable for storage in RAM 33. At preselected intervals when operating in what shall be called the "automatic operation" or "auto" mode, microprocessor 30 takes the instantaneous pH value as represented by the digital signal from A/D converter 29 and places its digital representation in the next consecutive unused memory location in RAM 33. Upon the conclusion of the study period, the contents of RAM 33 are communicated to computer 15, allowing for further analysis of the pH data. Since circuit 10 is in housing 41 carried by the patient, it should now be appreciated that the present invention allows the patient total mobility during the period of the pH study.

It has been known to be of great assistance in accurately analyzing reflux patterns observed during pH studies to know for all times pH data is recorded whether the patient is oriented upright or supine. Transducer 39 continuously and automatically furnishes this information as by altering the closure state of a set of contacts. Alternately the patient may manually enter positional information by switching the position of a switch.

Figure 3:
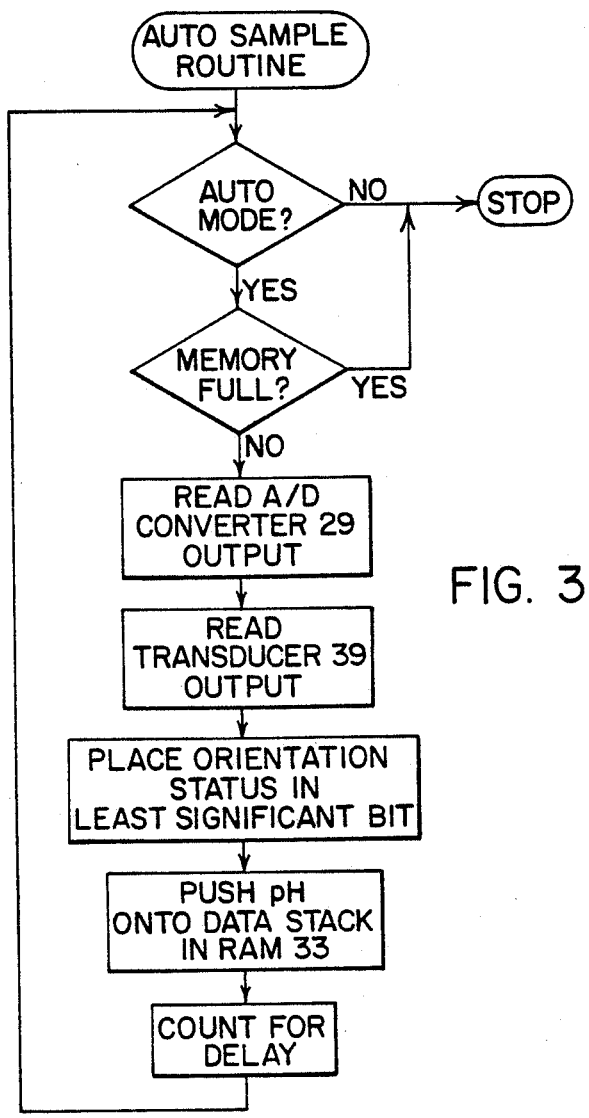
FIG. 3 is a flow chart of an automatic pH data sample routing executed by the portable pH monitoring device.

A flow chart for an acceptable auto sample routine to be carried out by processor 14 is illustrated in FIG. 3. Initially microprocessor 30 will check to see both that switch 38 is in the auto mode setting and that memory is not full. If either of these conditions is not met, auto mode operation stops. With both conditions met, microprocessor 30 gets the digital signal then in A/D converter 12, and checks the status of transducer 39. In accordance with a preselected convention to indicate orientation, a "1" or a "0" is placed in the first and least significant bit of each pH data byte, permitting more efficient utilization of RAM 33 memory space without deleterious loss of pH data resolution. Next, the entire pH data byte is placed in RAM 33 by pushing it onto the end of a memory block identified as "data stack". Microprocessor 30 then counts to a preselected number to delay for a preselected time, such as approximately 15 seconds, and repeats the auto sample routine.

Circuit 10 permits the use of any statistical correction procedure such as linear regression to correct for drift in the calibration of pH electrodes 18 and 19. To this end, both immediately before and after the pH study period the digital signals representative of several standard pH solutions (e.g., pH 1, 4 and 7) are stored in RAM 33. Upon the conclusion of the study period and transmission of the pH data to computer 15, computer 15 may suitably correct each pH value by any amount based upon these calibration values.

Recordal of three calibration values spread out over the range of possible pH values has been found sufficient to allow for appropriate statistical correction for electrode drift. To take into account variations introduced by the patient, reference pH electrode 19 should be cleaned and connected to the patient's skin, and one of the patient's fingers used in its stead throughout the pre- and post-calibration process now described. First, a voltmeter or other suitable calibration monitor 13 is connected to circuit 10 through terminals 43, and switch 38 set to the calibration mode. Esophageal pH electrode 18 and one of the patient's fingers are cleaned and inserted into a standardized solution having a known pH of, say, 1. The analog input voltage to A/D converter 29 is read from monitor 13 and signal offset control 23 adjusted until an arbitrarily selected magnitude, say, 1 volt, is obtained. Esophageal pH electrode 18 and the patient's finger are cleaned and inserted into a standardized solution having another known pH, this time of greater magnitude, as 4. Signal Gain Control 24 is adjusted until another arbitrarily selected magnitude of, say, 3 volts is achieved. Again, esophageal pH electrode 18 and the patient's finger are cleaned and inserted into a standardized solution having a third known pH, for example, 7. Signal offset control 23 and/or signal gain control 24 are adjusted until the third arbitrarily selected magnitude at the other end of the range of possible magnitudes is obtained.

This complete cycle is repeated several times until insertion of reference pH electrodes 18 and the patient's finger into all three standardized solutions yield the desired values, whereupon pushbutton 37 should be momentarily activated with reference pH electrode 19 and the patient's finger respectively inserted into each standardized solution, causing microprocessor 30 to store the three corresponding digital signals from A/D converter 29 in the first three memory locations in the RAM 33 data stack. Thereafter monitor 13 is removed, esophageal pH electrode 18 is cleaned and inserted into the patient, and switch 38 set to the auto mode, beginning the pH study period.

Upon the conclusion of the pH study period switch 38 is returned to the calibration mode, esophageal pH electrode 18 and the patient's finger are cleaned and sequentially inserted into standardized solutions of the same pH values as used in the pre-study calibration, and pushbutton 37 pressed to store the resulting digital signals from A/D converter 29. No adjustment must be made to signal offset control 23 or signal gain control 24. Thus, the first and last three digital signals stored in the data stack of RAM 33 will provide computer 15 with the extent of calibration drift in pH electrodes 18 and 19 during the pH study.

These calibration procedures ideally will be performed by the technician or medical personnel applying to the patient and removing from the patient pH electrodes 18 and 19. The skilled artisan will appreciate that microprocessor 30 may be programmed to automatically perform the pre-study iterative process utilized to achieve pH electrode calibration. Additionally, where the pH electrode pre- and post-study characteristics are known to remain stable, such as when using antimony electrodes, these calibration procedures may be eliminated.

At the conclusion of the pH study period and post-study calibration process the digital pH data may be transmitted to computer 15 connected to I/O interface 34. A multitude of techniques are known within the art for transmitting stored data between memory and a remote digital computer and any of these techniques may be utilized with circuit 10. For example, when computer 15 is connected to I/O interface 34, it may transmit an interrupt signal to microprocessor 30, causing communication to begin.

Once the digital pH data is received by computer 15, computer 15 performs a preselected regression analysis, corrects and plots the corrected pH data versus time for the entire pH study period. Additional patient identification and study information may be stored with the pH data and printed as a header to the plot. Computer 15 may perform further diagnostic analysis of the pH data, such as the well-known pH scoring approach promulgated by Johnson and DeMeester.

Several possible modifications to circuit 10 would occur to one of ordinary skill in the art. Clearly, by adjusting the delay period in the auto sample routine, pH data may be recorded at different intervals. Other software techniques are feasible for encoding patient orientation information, permitting the use of all 8-bits to resolve the magnitude of the instantaneous pH value of interest. Known data compression methods may be employed to increase the amount of data that may be stored in memory of a given capacity. For example, pH values may be recorded, together with the time relative to the start of the pH study period, only when the pH values change at least a preselected minimum. Several pH transducers may be multiplexed to allow recordal of bodily pH characteristics at several locations. Modulator/demodulator circuitry could be added to I/O interface 34 so that instead of directly connecting circuit 10 to computer 15, communication may be made over other indirect communication channels as telephone lines. Other transducers may be selected and utilized to record other bodily ionic concentrations such as $Na^+$, $Cl^-$, $K^+$, $HCO_3^-$ to name but a few that occur elsewhere in the gastrointestinal system.

Inasmuch as the present invention is subject to many variations, modifications and changes in detail, a number of which have been expressly stated herein, it is intended that all matter described throughout this entire specification or shown in the accompanying drawings be interpreted as illustrative and not in a limiting sense. It should thus be evident that a device constructed according to and method embodied within the concept of the present invention, and reasonably equivalent thereto, will accomplish the objects of the present invention and otherwise substantially improve the art of monitoring esophageal pH to obtain accurate reflux patterns.

We claim:

1. A circuit for monitoring over a period of study time a bodily ionic characteristic comprising:
    transducer means for measuring the ionic characteristic and generating an analog signal proportional thereto;
    interface means for receiving said analog signal from said transducer means and converting said analog signal into a representative digital signal, said interface means including adjustment means for permitting variable correction for drift in calibration of said transducer means occurring during the period of study time; and,
    processor means for receiving said digital signal, sampling said digital signal at preselected occasions over the study period, and storing said sampled digital signal for subsequent data analysis.

2. A circuit, as set forth in claim 1, further including housing means for portably carrying said interface means and said processor means, said transducer means operatively connected to said interface means.

3. A method for monitoring over a period of study time a bodily ionic characteristic comprising the steps of:
    determining the ionic characteristic for a plurality of pre-study conditions and recording first digital signals representative thereof;
    measuring by transducer the ionic characteristic throughout the study period and at preselected occasions recording second digital signals representative thereof;
    determining the ionic characteristic for a plurality of post-study conditions and recording third digital signals representative thereof;
    providing said first digital signals, said second digital signals and said third digital signals to a data analysis device; and,
    correcting said measured ionic characteristic for variable drift in calibration of said transducer occurring during the period of study time.

4. A method, as set forth in claim 3, wherein said step of measuring the ionic characteristic throughout the study period includes the steps of measuring with a transducer the ionic characteristic and generating an analog signal proportional thereto throughout the study period, converting said analog signal into said second digital signal, and, sampling and storing said second digital signal at preselected occasions during the study period.

5. A method, as set forth in claim 4, wherein said step of determining the ionic characteristic for a plurality of pre-study known conditions includes the steps of measuring with a transducer prior to commencement of the extended period of time the ionic characteristic and generating an analog signal proportional thereto for a plurality of pre-study known conditions, converting said analog signals for said plurality of pre-study known conditions into said first digital signals, and, storing said first digital signals representative of said plurality of pre-study known conditions.

* * * * *